DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED APRIL 2, 1974

921 O.G. 9

T921,002

PROCESS FOR PRODUCING BUTYLATED HYDROXYANISOLE AND HIGH 3-ISOMER CONTENT

James Michael Coe, 2152 Swannanoa Ave., and Charles Edward Osborne, 1540 Belmeade Drive, both of Kingsport, Tenn. 37664

Continuation of application Ser. No. 156,131, June 23, 1971. This application Dec. 22, 1972, Ser. No. 317,560

Claims priority, application Great Britain, June 23, 1972, 29,614/72

**Int. Cl. C07c *43/20***

U.S. Cl. 260—613

No Drawing. 7 Pages Specification

Process for preparing butylated hydroxyanisole (BHA) of high 3-isomer content, comprising providing an agitated reaction system of t-butylhydroquinone and dimethyl sulfate in an organic solvent and a limited amount of water, and slowly adding thereto aqueous sodium hydroxide or other hydroxide over a period of from about 1 to about 3.5 hours while maintaining the system at a relatively low temperature of from about 30 to 50° C., the total amount of water in the reaction system being from about 2.5 to about 5 parts per 10 parts of dimethyl sulfate, the amount of dimethyl sulfate being from about 1 to about 3 moles per mole of hydroxide, and the t-butylhydroquinone being in slight excess of from about 0.1 to about 0.5 mole per mole of hydroxide.